United States Patent [19]

Martin

[11] Patent Number: 4,673,407

[45] Date of Patent: Jun. 16, 1987

[54] JOINT-REPLACEMENT PROSTHETIC DEVICE

[76] Inventor: Daniel L. Martin, One St. Francis Place, Apt. 1107, San Francisco, Calif. 94107

[21] Appl. No.: 704,622

[22] Filed: Feb. 20, 1985

[51] Int. Cl.[4] .............................................. A61F 2/38
[52] U.S. Cl. ...................................... 623/20; 623/18
[58] Field of Search .................... 3/1.9, 1.91, 1.911, 3/1.912, 1.913; 128/92 C, 92 CA, 92 B, 92 BA, 92 D

[56] References Cited

U.S. PATENT DOCUMENTS

| | | | |
|---|---|---|---|
| 4,000,525 | 1/1977 | Klawitter et al. | 3/1.91 |
| 4,129,903 | 12/1978 | Huggler | 3/1.913 |
| 4,530,114 | 7/1985 | Tepic | 128/92 CA |

FOREIGN PATENT DOCUMENTS 2078528  1/1982  United Kingdom ....................... 3/1

*Primary Examiner*—Richard J. Apley
*Assistant Examiner*—David Isabella
*Attorney, Agent, or Firm*—Ciotti & Murashige

[57] ABSTRACT

A prosthetic device for use in joint replacement in a bone. The device includes an implant adapted to seat on a receiving surface of the bone, defining a bone/implant interface, and an attachment element adapted to be secured to a portion of the bone which is spaced from the interface by an axially extending bone region. The implant is connected to the attachment element by a connecting member adapted to allow substantially unhindered movement of the implant relative to the attachment member to freely accommodate elastic deformation in the bone region between the implant and attachment element. A low-modulus spring, operatively interposed between the connecting member and the implant or attachment element, functions to hold the implant against the bone surface with a selected compression force.

6 Claims, 9 Drawing Figures

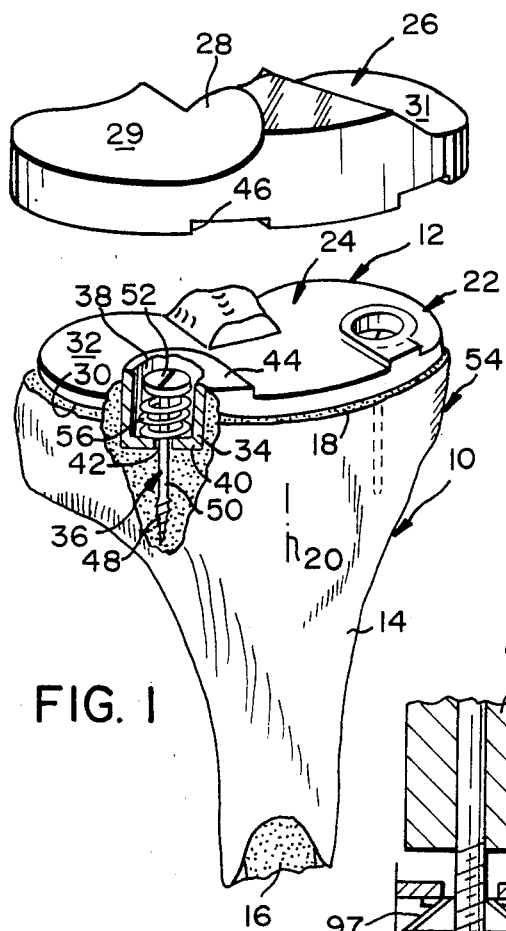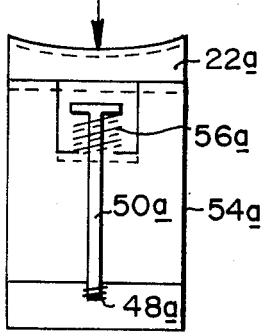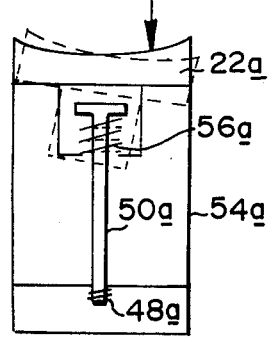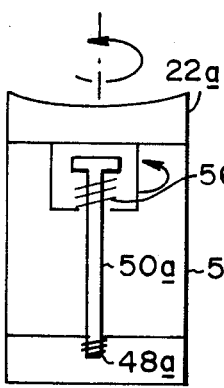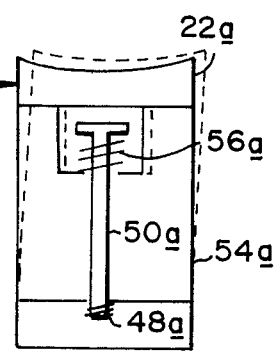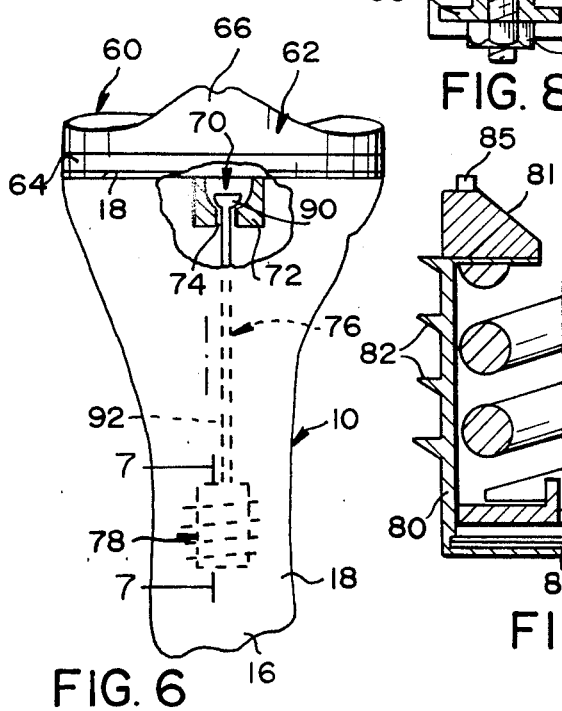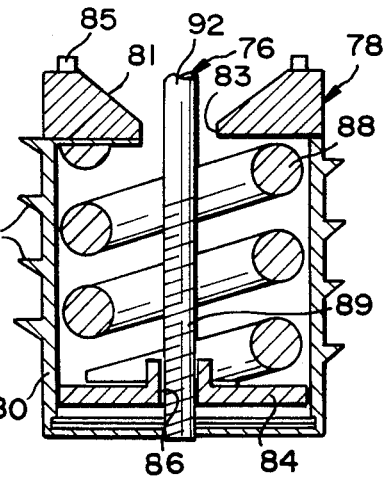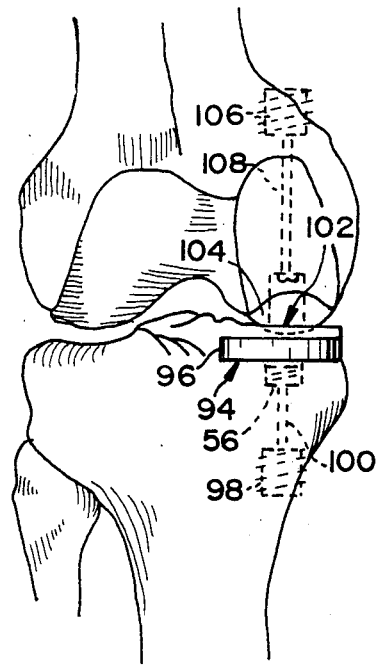

JOINT-REPLACEMENT PROSTHETIC DEVICE

FIELD OF THE INVENTION

The present invention relates to a joint-replacement prosthetic device, and in particular to a prosthetic device for use in knee-joint and hip-joint replacement.

BACKGROUND OF THE INVENTION

Hip-joint or knee-joint replacement is a widely used orthopedic procedure to correct various types of joint injury, such as those caused by osteoarthritis, fracture dislocations, rheumatic arthritis, and aseptic bone necrosis. A variety of prosthetic devices for hip and knee-joint replacement are known. The usual device used in femoral-side hip-joint replacement includes an elongate stem having a ball-like joint implant formed at one end. The stem is constructed for insertion into the medullary region of a femur adjacent the joint, and may be secured in the medullary region by a grout material, such as methylmethacrylate. In time, the bone reacts to the grout material or smooth metal stem by forming a soft-tissue lining around the stem, and this lining mediates load transfer from the prosthetic device to the bone.

This type of prosthetic device has not been entirely satisfactory, particularly in active younger patients, where it is important to form a stable, long-lasting prosthetic attachment. The soft-tissue lining that forms about the device tends to loosen over time, particularly with continued shear loads, i.e., loads applied substantially in the direction of the axially extending bone/stem interface, and the loosening may become great enough in time to require surgical revision. Also, the relatively low tolerance of force transfer per unit area of interface requires a large bone/stem interface, which, in younger patients, may exceed the available bone stock.

The problems associated with anchorage via soft tissue along a prosthesis stem have been overcome partially by using a prosthesis whose stem surface allows direct attachment without an interposed soft tissue layer. Such surfaces include micropore surfaces that allow attachment via ingrowth and/or attachment of bone, and ceramic surfaces that allow actual bonding of bone. Following surgical implantation of the stem, the surrounding bone tissue gradually forms a biological fixation matrix with the stem surface by tissue growth into or onto the surface. Because of the stronger interface between the bone and the stem, which allows a relatively large force per unit area without loosening, problems of loosening and detachment are largely avoided and the force transfer area can be made smaller.

A limitation of the biological-fixation bonding approach, however, is the need to keep the prosthesis mechanically fixed with respect to the bone over a 2-3 month post-operative period, during which the biological fixation is occurring. If relative movement between the implant stem and bone is allowed to occur before biological fixation is complete, a fibrous tissue layer which acts to prevent good biological fixation develops at the interface and progression to gross loosening is likely.

Another limitation of prosthetic devices which rely on biological fixation, particularly fixation to an elongate stem within the intramedullary region of a bone, is the problem of stress protection of the bone region between the area of force application to the prosthesis and the area of load transfer to the bone. Stress protection is due to the rigid attachment between the prosthetic device and bone which occurs in biological fixation and to the relatively high elastic modulus of the implant material, which typically is 5-15 times greater than that of the surrounding bone. These two factors combine to transfer a stress from the area of stress loading on the implant through the more rigid implant, rather than through the surrounding bone tissue. For example, in a hip-joint prosthesis biologically anchored to the bone by an entire elongate stem, axial stress on the upper joint is transferred largely through the stem to the bone connection farthest from the joint, rather than through the intermediate bone region surrounding the part of the stem closest to the joint. As a result, the intermediate bone region tends to be resorbed over time due to a lack of deformation stressing. The gradual loss of bone support in the region of the stem increases the bending load that must be borne by the stem, and this can lead to implant fatigue and failure.

The problem of maintaining a motionless bone-prosthesis interface during the post-operative period when bony attachment is occurring may be partially solved by surgically fastening the prosthetic device to the bone structure by screws or the like. This method has been proposed for use in fastening a knee-joint prosthesis to a surgically formed, substantially planar surface of the bone. Typically, the prosthesis is attached by two or more screws, each tightened to hold the prosthesis against the bone surface with a selected compression. However, since the bone quickly accommodates to the applied force of the screws, by viscoelastic creep, the compression, and thus the resistance to the implant movement relative to the bone, is quickly lost. If interface movement does occur from a single episode of overloading, then any residual compression is permanently lost. More movements result in build-up of fibrous tissue, preempting biological bone fixation to the implant. Only with unphysiologic post-operative protection of the joint, resulting in joint stiffness and muscle wasting, and with demanding operative technique, can this risk of loosening be reduced to safe level. The device also suffers from problems of stress protection and non-physiological load transfer, inasmuch as loading force applied to the prosthesis is transferred directly through the screws, rather than through the region of bone through which the screws extend. This can lead to loss of bone integrity in the stress protected area.

Prosthetic devices having spring-loaded mechanisms for holding a joint-replacement prosthesis against a planar surface of the bone, to immobilize the prosthesis on the bone, have been proposed, e.g., in U.S. Pat. No. 4,129,903. Devices of this type solve some of the above-noted problems associated with prosthesis attachment to the bone, in that the prosthesis is held against the bone under relatively constant tension in the post-operative period, with or without provision for biological fixation. Nonetheless, limited movement may occur when the major loading stresses (in the principal direction of weight transfer on the joint) are not normal to the plane of the interface between the bone and prosthetic device and it is necessary to rely on a grouting compound to prevent shear motions. Further, such devices use a rigid stem or shaft for anchoring the implant to the bone, substantially stress protecting the bone traversed by the stem from physiologic shear, rocking, and/or axial rotation stresses.

SUMMARY OF THE INVENTION

It is therefore a general object to provide an improved joint-replacement prosthetic device which solves or minimizes the above-discussed problems associated with prior art prosthetic devices.

More specifically, the object of the invention is to provide such a device embodying the advantages of:

(a) substantially physiological load transfer from the device to the supporting bone, particularly where the device is formed of a high-modulus material such as metal; entailing where practical, a planar interface normal to the direction of greatest loading on the joint;

(b) load transfer from the device to the bone near the joint; and (c) immediate, rigid and durable attachment of the device sufficient to withstand stresses from full range-of-motion exercises in the post-operative period.

Providing such a device which is readily installed surgically is yet another object of the invention.

The prosthetic device of the invention is for use in joint replacement in a bone. The device comprises, when operatively assembled, an implant adapted to seat on a receiving surface of the bone and defining an interface therewith, and an attachment element adapted to be secured to a portion of the bone which is spaced from the interface by a generally axially extending bone region. A connecting member connecting the implant to the attachment area is adapted to allow substantially unhindered movement of the implant relatively to the attached member, to accommodate elastic deformation in the bone region. The connecting member thus allows substantially physiological loading of the bone in the region between the implant and the attachment member. A low modulus spring operatively interposed between the the implant and the attachment element is adapted to hold the implant against the bone surface with a selected compression force, high enough to immobilize the prosthetic device with respect to the bone surface, and to expand slightly to accommodate viscoelastic creep and overload episodes and still maintain compression. Preferably, the implant/bone-surface interface is substantially planar, and the compression force and major loading forces act in directions which are substantially normal to the interface plane.

In one general embodiment, the attachment element is a plug designed for placement in the intramedullary or other region of the bone, and the low-modulus spring is contained already partially compressed within the plug to hold the connecting member under tension. The connecting member preferably has a bending modulus whose contribution to total elastic modulus of the bone region containing the member is quite small.

In a second general embodiment, the attachment member is the threaded end portion of a screw adapted to be secured in the bone, and the connecting member is the shaft portion of the screw which terminates in an enlarged-diameter head. The head is received within a cavity in the prosthesis for sliding and lateral movement therein. The low-modulus spring is interposed between the cavity floor and the screw head to bias the implant toward the screw's threaded attachment to the bone.

These and other objects and features of the present invention will become more fully apparent when the following detailed description of the invention is read in conjunction with the accompanying drawings.

BRIEF DESCRIPTION OF THE DRAWINGS

FIG. 1 is an oblique view of a knee-joint prosthetic device constructed according to one embodiment of the invention, and shown operatively attached to a tibia;

FIGS. 2-5 illustrate schematically various types of elastic deformation which can occur in the region of the bone adjacent the joint, including compressional movement along the long axis of the bone (FIG. 2), differential compression on opposite side regions of the joint, resulting in a rotational movement about an axis normal to the bone axis (FIG. 3), rotational or twisting movement about the bone axis (FIG. 4), and shear movement which is substantially normal to the bone axis (FIG. 5);

FIG. 6 shows a knee-joint prosthetic device constructed according to another general embodiment of the invention;

FIG. 7 is an enlarged sectional view of an attachment member and low-moculus spring in the device of FIG. 6, shown generally along line 7—7 in that figure;

FIG. 8 shows an enlarged sectional view like FIG. 7, of an attachment element and associated connecting member with an elastomeric sleeve and associated Belleville washer-type spring, and a nut as an alternative means for compressing the spring; and FIG. 9 shows a partial knee-joint replacement device constructed according to yet another embodiment of the invention.

DETAILED DESCRIPTION OF THE INVENTION

FIG. 1 shows a knee-joint portion of a tibia bone 10 whose lower knee joint has been replaced by a prosthetic device 12 constructed according to one embodiment of the invention. The hard outer-surface cortical region of the bone is indicated at 14, and the softer intramedullary region is indicated at 16 in the figure. The bone is prepared for joint replacement by surgically removing the joint and forming near the joint region a substantially planar receiving surface 18 which defines a plane normal or substantially normal to the bone's long axis 20. It is noted here that a prosthetic device of the invention may be constructed for receipt on a receiving surface composed of a series of planar facets, including the principal one whose plane is preferably normal to the bone's long axis. Surgical procedures for preparing a planar (or faceted) receiving surface on a bone are well known in orthopedic surgery.

Device 12 includes a joint-replacement implant 22 composed of a inner plate member 24 and outer joint member 26, whose outer surface 28 defines a pair of joint surfaces 29, 31 in the device. Plate member 24 is a plate-like structure whose lower (inner) surface 30 is adapted to be held against the bone-receiving surface, and whose upper (outer) surface 32 is constructed for interfitting with a complementary-fit surface of the joint member. The lower surface of the plate member is adapted to promote biological fixation of the receiving surface of the bone to the plate member by bone tissue growth.

The plate member has spaced wells, such as well 34 seen cross-sectionally in the figure, each of which receives the head region of a screw, such as screw 36, used in attaching the implant to the bone. Well 34, which is representative, forms a cavity 38, which is closed at its lower end in the figure by a cap 40. Screw 36 is received through a central opening 42 in the cap. According to an important feature of the invention, the cavity and opening 42 therein are dimensioned to allow relative axial and lateral movement of the screw with respect to the implant, for a purpose to be described.

Components 24 and 26 interfit snugly via complementary-fit recesses after the inner plate 24 is fully mounted on the bone 14, so as to prevent relative movements.

The plate and joint members may be formed of any biocompatible material with appropriate wear, strength, fatigue, and cold flow characteristics, such as titanium or cobalt-chromium alloys, and polymers. They are cast, machined, or molded, as an integral article. Typically the components placed in direct contact with bone are metal, with a material elastic modulus 5-15 times the adjacent supporting bone. As will be seen below, one of the advantages of the invention is that the problems of the differences in modulus between the implant and bone are largely minimized by the manner in which the implant device is mounted and interacts with the bone. The biologic fixation structure on the inner surface of the plate member is formed conventionally, such as by sintering small metal beads or wire mesh onto the surface, or by adhering a ceramic layer.

With continued reference to FIG. 1, screw 36, which is representative, includes a lower threaded portion 48, a central shaft portion 50 and an enlarged diameter head 52. The threaded portion of the screw is adapted to be anchored to the bone, for example, by being screwed into the hard cortical region of the bone, as shown. The threaded portion is also referred to herein as an attachment element adapted to be secured to a portion of the bone which is spaced from the interface between the bone and the plate member by a generally axially extending bone region, shown here at 54. The central shaft portion of the scew, which extends through the just-mentioned bone region and into cavity 38, and the enlarged-diameter head are also referred to herein as a connecting member. As indicated above, the relative dimensions of the screw and cavity allow limited, unhindered axial and lateral movement of the connecting member with respect to the implant. The manner in which this unhindered relative movement permits substantially physiological load transfer from the implant to bone region 54 will be seen below.

Operatively interposed between the connecting member in each screw and the implant is a compression spring, such as spring 56 associated with screw 36. It can be appreciated that compression in the spring acts to bias the plate member against the bone-receiving surface, at a selected tension which depends upon the spring rate (change in load per unit deflection) and extent of compression in the spring. According to one important feature of the invention, the spring compression is selected to hold the implant against the bone receiving surface with a selected compression force which by way of friction effectively prevents relative lateral movement of the implant on the bone surface, particularly in the post-operatiave period before tissue fixation has occurred. That is, the spring acts to immobilize the implant on the bone surface to prevent the kind of lateral movement which would otherwise induce fibrous tissue formation at the implant/bone interface and prevent effective bone fixation to the implant. According to another key feature of the invention, stress protection of bone is avoided by selecting a spring with a relatively low rate. The total spring rate for the section spanned by the connecting member equals the sum of the spring's rate plus the axial spring rate of the entire bone segment. An axial load change applied to the prosthesis is distributed between the (1) bone and (2) spring-connecting member unit according to their contributions to the total spring rate. A spring is chosen, therefore, which has a rate low in comparison to the axial spring rate of the whole bone section spanned by the connecting member. In this way, the bone underlying the prosthesis sustains the majority of the axial load change, even though it is being spanned by an axially rigid connecting member. If the spring contributes only 2% or 10% to the total axial spring rate, the bone sustains 98% or 90% of applied axial load changes, much more than in prosthetic systems without a spring interposed between the prosthesis and its farthest point of attachment. With an interposed elastic element, the connecting member does not constrain force transfer directly from the planar interface to the subjacent bone, avoiding stress protection. Similarly, a rigid connection of a thick stem to the subarticular portion of the prosthesis prevents direct transfer of physiologic shear, rocking, and axial rotation forces (FIGS. 3-5) to the bone closest to the joint. A key object of this invention is to avoid constraining the transfer of physiologic forces from the subarticular portion of the prosthesis to the adjacent bone.

The spring has a rate low in comparison to the axial spring rate of the bone, and low in comparison to other conventional connecting elements such as rigid stems and screws to provide compression. The compression, or pre-stress, applied to the interface is transmitted through the low rate spring element, and therefore one could refer to it as "low modulus pre-stress", to distinguish it from systems which apply interface pre-stress with rigid, or high modulus, connecting elements. This difference is key to the invention.

The device is surgically attached to bone 10 by first fashioning the bone surgically to provide a planar, plate-receiving surface. The plate member is then attached to the surface by screws, such as screw 36, these being tightened into the bone until a desired load on the springs is achieved. The joint member is then secured to the plate member conventionally.

FIGS. 2-5 illustrate, in schematic form, the response of the prosthetic device to four basic types of elastic deformation which can occur in the bone, associated with physiological load transfer from the implant to the bone. In each figure, the implant is shown at 22a, and the attachment element, corresponding to the threaded screw portion of the attachment screws in device 12, at 48a. The implant if connected to the attachment element by a connecting member 50a corresponding to the shaft and head portions of the attachment screws in device 12 and is held against the bone by a spring 56a interposed between the connecting member and the implant. The axially extending region of the bone between the implant and attachment member is shown at 54a. FIG. 2 shows, in exaggerated scale with dotted lines, movement of the implant with respect to the attachment member in response to axial compression of the bone produced by an axial load acting on a central portion of the implant. As seen in the figure, compression in the bone region between the implant and the attachment element is accommodated by axial movement of the screw in the implant cavity, and a corresponding expansion in spring 56a.

In FIG. 3, a vertical load is applied to a side region of the implant, producing greater load compression on one side of the bone than on the other. The net effect, again shown in exaggerated scale in dotted lines, is to rotate the implant about an axis, which is normal to the plane of the figure. The relative movement between the implant and the attachment member here is accommodated by both axial and lateral movement of the connecting member with respect to the implant, the lateral movement being accomodated by the clearance between the connecting member and the opening in the implant cavity, as seen. As in FIG. 2, the only load-resistance contributed by the implant device is that resulting from slight compressional changes in the spring.

FIG. 4 illustrates twisting movement of the implant with respect to the attachment element, about the axis of the shaft. This movement is accommodated by the rotation of the implant about the head of the screw, and by a torsional deflection in the spring.

FIG. 5 shows the effect of a hypothetically pure shear force applied to the implant in a direction perpendicular to the axis of the bone. As seen in exagerated scale in dotted lines, the shear load produces a net bending effect in bone region 54a, this bending being accommodated primarily by lateral shifting of the connecting member with respect to the implant cavity.

Although the various types of load-response elastic deformation movements which can occur in a bone have been described separately, it is understood that typically a load applied to the implant will contain vector components which produce two or more types of composite elastic deformation movement in the bone, such as compression and twisting, or compression and shearing. Similarly, the response of the device in accommodating composite elastic deformation in the bone region is just a composite of the various types of implant responses which have been described individually for each separate component of elastic deformation. For example, in combined compression and shearing deformation, relative axial movement of the screw head within the well and relative lateral movement of the shaft with respect to the well opening will provide the requisite low-modulus response to the composite deformation.

It will also be appreciated from FIGS. 2-5 that the greatest loading of the implant on the bone will be in the direction weight loading—in the implant illustrated, substantially parallel to the bone's longitudinal axis. According to a preferred construction of the invention, the interface between the implant and the bone-receiving surface lies in a plane which is substantially normal to the direction of loading. This plane orientation minimizes the shear forces applied to the implant/bone interface and thus cooperates with the spring to restrict lateral movement of the implant on the bone in the early post-operative period. The normal planar configuration also distributes the applied force over the interface more evenly than any other interface configuration.

A second general embodiment of an implant device, for use as a lower knee-joint replacement, is indicated generally at 60 in FIG. 6. The bone, including its outer cortical and inner intramedullary regions, and generally planar implant-receiving surface, are designated by the same numbers as in FIG. 1. Device 60 generally includes an implant 62 composed of an inner plate member 64, which is adapted to be attached to the bone in the manner to be described, and a detachable outer joint member 66 defining articular bearing surfaces. The joint member is constructed to receive the complementary shaped plate member, much as described above with respect to FIG. 1.

The plate member is provided with a single central well 70, which is shown in cutaway view in the figure. The well, like the wells in device 12, provides a cylindrical cavity which terminates at its lower end in the figure with a cap 72, providing an opening 74 dimensioned to receive the shaft of a connecting member 76 therethrough. The inner surface of the cap provides a concave surface which forms the socket in a ball-and-socket joint between the implant and the connecting member, to allow swinging movement of the connecting member with respect to the well, as will be described. The opening 74 in the well is dimensioned to accommodate slight swinging movement of the connecting member with respect to the well about an axis substantially normal to the axis of the connecting member.

The attachment element in the device used in attaching the implant to the bone is a plug 78 which is threaded for screw-type anchoring in the intramedullary portion of the bone, as shown. Details of the plug are seen in FIG. 7, which shows the plug in an enlarged, sectional view. As seen, the plug includes a generally cylindrical housing 80 having outer screw threads, such as threads 82, for use in fastening the plug to the bone. The upper end of the housing in the figure defines a frusto-conical surface 81 used in guiding the connecting member into the upper opening 83 in the plug. A pair of protuberances 85 on the upper end are used in gripping the plug when tightening the plug in the house. A thrust plate 84 in the plug is dimensioned for rocking movement and sliding movement within the housing to and away from the lower end of the housing. The plate has a central threaded bore 86 adapted to receive the threaded end of connecting member 76 in the manner shown.

A spring 88, contained within the plug housing functions to bias the thrust plate toward the lower end of the plug, to maintain a desired tension in the connecting member. The spring thus operatively connects the plug housing to the implant, through tension in the connecting member.

With reference again to FIG. 6, the connecting member is an elongate bolt having a lower threaded portion 89 seen in FIG. 7, which is adapted for threaded attachment to the thrust plate 84. The bolt terminates at its upper end in an enlarged-diameter head 90, whose lower surface in the figure has a spherical convex shape which forms the ball surface in the above-mentioned ball-and-socket connection between the implant and the connecting member. The elongate shaft portion of the connecting member, shown in dotted lines at 92 in FIG. 6, extends substantially through the region of bone between the implant interface and the attachment element. The shaft portion is formed of a metal rod having a bending stiffness of less than 1/10 that of the spanned bone region to accommodate certain types of elastic deformation in the bone, to be described.

The implant device is attached to bone 10 by first fashioning the bone surgically to provide a planar, plate-receiving surface and removing intramedullary portions of the bone necessary to screw the plug into the bone. The plug is screwed into the bone by means of a wrench adapted to engage the protuberances on the upper end of the housing. After anchoring the plug in the bone, the plate member is placed against the bone receiving surface, and the connecting member is inserted through the opening in the plate-member well, through the bone until the lower end of the threaded region is received in the plug. It can be appreciated how the funnel shaped upper-end portion of the plug acts to guide the bolt tip into the plug during this procedure. The connecting member is then threadedly engaged with plate 84 in the plug and tightened until tension in spring 88 holds the implant with a desired compression against the bone. It is seen that a connecting member can be relatively thin and flexible, since high-torque forces are not needed to attach the connecting member to the plug. With the plate member secured to the bone at a desired spring tension to hold the implant against the bone with a selected compression force, the joint member is fastened to the plate member.

The functioning of the connecting member in allowing substantially unhindered movement of the implant relative to the plug, to accommodate elastic deformation in the bone region between the plug and the implant, will now be considered. Axial compression movement, such as that illustrated in FIG. 2, is readily accommodated by slight expansion of the low-modulus spring carried in the plug, similar to the response of device 12 to compressional deformation. Rotational movement of the type illustrated in FIG. 3, due to asymmetric compressional forces applied to the implant, produces both a slight rotational shifting of the implant about the connecting member, which is accommodated by the ball-and-socket connection between the two, and a slight movement of the center portion of the implant toward the plug, which is accommodated by axial deflection in the spring. Twisting deformation in the bone is, as in device 12, accommodated by relative rotation of the implant with respect to the connecting member, accommodated at either or both ends of the cnnecting member. Finally, shearing movement such as illustrated in FIG. 5, is accommodated by a slight swinging movement in the wide opening made during insertion of the plug, or, if this hole is eventually filled in with bone, a slight bending of the connecting member in the direction of the applied shear force.

From the above discussion, it can be appreciated that the features of the connecting member which allow it to accommodate deformation in the bone region through which the connecting member extends are (1) the ball-and-socket attachment to the implant, (2) the flexibility in the connecting member shaft, and (3) the axially and rotationally moveable thrust plate linked to the connecting member. As seen from the described functioning of device 12 above, a flexible connecting arm is not required where the coupling of the connecting arm to the implant allows both unhindered axial and lateral movement. Similarly, the connecting member can be rigidly attached to the implant where the connecting member is sufficiently flexible to provide a relatively low-modulus deformation response to tilting or shearing or twisting movements of the implant with respect to the plug.

FIG. 8 shows another embodiment of a prosthetic device having a plug-type attachment element 93. Here the thrust plate 95 is biased in a downward direction by a pair of confronting (stacked) Belleville washers 97. The washers may be selected to display flat or even negative slopes in portions of their load-deformation curves, and thus can make a zero contribution to the total axial spring rate, while maintaining a high compression force. This totally eliminates the stress protecting effect while maintaining interface compression. The FIG. 8 device also includes a connecting member having a sleeve 99 which has a material modulus much lower than the adjacent metal or bone. This sleeve serves to mechanically insulate the connecting member from the bone, eliminating any need for the connecting member itself to be flexible. FIG. 8 also shows a nut 107 applied to the end of the threaded connecting member shaft, as an alternative means for applying compression to the interface.

Yet another embodiment of the invention is shown in FIG. 9, which illustrates a pair of interactive joint replacement devices for replacing one of the three major joint compartments in a knee. A lower knee-joint device 94 may have substantially the same construction as device 60, including a two-member implant 96 anchored to the right side of the bone by means of a plug 98, which is screwed into and through the cortical region of the bone. The implant is connected to a plug not containing an elastic element through a connecting member 100, in this case with a spring 56 between the screw head and cavity floor to allow substantially unhindered movement of the implant with respect to the attachment member, and to accommodate elastic deformation of the bone region between the implant and the plug. The spring operates to hold the implant against the bone/implant interface surface with a selected compression force. Similarly, an upper knee-joint prosthetic device 102 has an implant 104 whose surface is in joint contact with implant 96 to provide a complete replacement of one conpartment in the knee joint. The upper device implant is mounted on the bone through a plug 106, which is also anchored in and extends through a cortical region of the bone directly above the implant. The implant is anchored to the plug through a flexible connecting member 108, which is coupled to the plug through a low-modulus spring. Each device functions as described above to achieve substantially physiological loading between the implant and associated bone structure by permitting substantially unhindered movement of the implant relative to the attachment member to accommodate elastic deformation in the bone structure between the implant and its attachment element. In addition, the two devices illustrate anchoring of an attachment element into and through cortical sections of the bone, and confronting interactive prosthetic devices which are intended to replace only a portion of a joint.

From the foregoing, it can be seen how various objects and features of the invention are met. The device is relatively easily attached to a bone surface by first preparing a planar or other technically easy-to-produce surface on which the implant is to be received, and fastening an attachment member, such as a plug or a screw, to an underlying region of the bone. The low-modulus spring through which the implant is coupled to the atachment element, biases the implant against the bone with a selected compressive force which acts to maintain the implant in a stationary position with respect to the bone. The spring thereby acts to prevent movement of the implant with respect to the bone, reducing the likelihood of fibrous-tissue formation at the interface, which would otherwise interfere with bone fixation to the biologic fixation surface of the interface, at the same time allowing a relatively greater amount of early post-operative range of motion exercise in the joint in the period immediately after surgical joint replacement without risk of implant loosening. The amount of lateral motion which can occur between the implant and bone is further restricted where, as preferred, the plant of interface between the bone and implant is substantially normal to the primary loading forces which are applied to the joint, and also normal to the direction of action of the low-modulus spring.

The connecting member in the device, either by virtue of its flexibility and/or the degrees of freedom allowed by the coupling between the connecting member and the implant and the attachment element, is adapted to accommodate compressive, rotational, twisting, and shearing deformation in the bone in a manner which provides substantially physiological bone loading. That is, the transfer of forces from the joint to the bone occurs near the joint surface such that in the bone near to articular or joint portion of the prosthesis, the stresses are nearly the same as if the end of the bone were covered by a normal joint.

While preferred embodiments of the invention have been described herein, it will be apparent that various changes and modifications can be made without departing from the invention. For example, the implant may be provided with a relatively short stem, particularly for use in a hip-joint replacement implant, where the stem functions to resist cantilever load applied to the prosthesis mechanism. The lower portion of the stem may be provided with a low-modulus material such as in the previously described sleeve, which allows mechanical insulation of the stem from the surrounding bone tissue, after biologic fixation occurs at the appropriate interface near the joint. The stem and interface are anchored into the bone by connecting an attachment member such as an intramedullary plug to the implant.

It is claimed:

1. A prosthetic device for use in joint replacement in a bone, comprising, when operatively assembed.

an implant defining an interface surface adapted to seat on a receiving surface of the bone, an attachment element adapted to be secured to a portion of the bone which is spaced from such interface by an axially extending bone region, a connecting member, connecting the implant to the attachment element, adapted to allow substantially unhindered axial, lateral, rotational, and twisting movement of the implant relative to the attachment member, to produce substantially physiological loading of such bone region in response to compressional, shear, rotational and twisting forces, respectively, which are applied to the implant, and a spring (i) having a spring rate which is low in comparison to the spring rate of the bone region spanned by the connecting member, and (ii) operatively interposed between the implant and the attachment element, for biasing the implant against such surface with a selected compression force that is directed substantially parallel to the principal force application to the joint, and which exerts substantially no shear force on the implant, wherein said attachment element is a plug adapted for anchoring to such bone portion, and the spring element is contained in the plug.

2. The device of claim 1, wherein the plug includes a housing and a plate mounted within the housing for sliding movement toward and away from the implant, said spring is interposed between the housing and the plate to resist plate movement toward the implant, and said connecting member is connected to the plug by attachment to the plate.

3. The device of claim 2, wherein the connecting member is an elongate flexible shaft.

4. A prosthetic device for use in knee-joint replacement comprising, when operatively assembled, an implant adapted to seat on a receiving surface of the bone, defining a substantially planar interface thereon, and having spaced cavities each of which communicates with the implant surface forming such interface, for each cavity, a screw having a threaded end portion adapted to be secured to a portion of the bone which is spaced from such interface by an axially extending bone region, and, forming an extension of the threaded end portion, a shaft adapted to extend through such bone region, terminating at an enlarged-diameter head which is received in the associated implant cavity, for sliding and lateral movement therein, and for each cavity, a spring operatively interposed between the cavity and the associated head for resisting movement of the implant away from the attachment element.

5. The device of claim 4, wherein the implant includes a plate member defining such cavities, adapted to seat on such receiving surface, and a joint member forming the joint surface in the implant and adapted to be rigidly secured to the plate member.

6. the device of claim 4, wherein the connecting member includes a sleeve made of a material with a low elastic modulus.

* * * * *